(12) United States Patent
Zhou (10) Patent No.: US 9,451,793 B2
(45) Date of Patent: Sep. 27, 2016

(54) MINI-DOUBLE FLAVOR ELECTRONIC CIGARETTE

(71) Applicant: SHENZHEN BAUWAY TECHNOLOGY LIMITED, Baoan Dist., Shenzhen, Guangdong (CN)

(72) Inventor: Xuewu Zhou, Guangdong (CN)

(73) Assignee: SHENZHEN BAUWAY TECHNOLOGY LIMITED (CN)

( * ) Notice: Subject to any disclaimer, the term of this patent is extended or adjusted under 35 U.S.C. 154(b) by 88 days.

(21) Appl. No.: 14/516,756

(22) Filed: Oct. 17, 2014

(65) Prior Publication Data

US 2015/0164145 A1 Jun. 18, 2015

(30) Foreign Application Priority Data

Dec. 13, 2013 (CN) .................... 2013 2 0827884 U (51) Int. Cl.
*A24F 47/00* (2006.01)
*A61M 15/06* (2006.01)
*A24D 1/00* (2006.01)

(52) U.S. Cl.
CPC ............ *A24F 47/008* (2013.01); *A61M 15/06* (2013.01); *A24D 1/002* (2013.01)

(58) Field of Classification Search
CPC .... A24F 47/00; A24F 47/002; A24F 47/004; A24F 47/006; A24F 47/008
See application file for complete search history.

(56) References Cited

U.S. PATENT DOCUMENTS

| | | | | |
|---|---|---|---|---|
| 2012/0260927 A1* | 10/2012 | Liu | ................. | A24F 47/008 131/329 |
| 2013/0340778 A1* | 12/2013 | Liu | ................. | A24F 47/002 131/329 |
| 2014/0000638 A1* | 1/2014 | Sebastian | ............. | A24F 47/008 131/328 |
| 2014/0060527 A1* | 3/2014 | Liu | ................. | A61M 15/06 128/202.21 |
| 2014/0060556 A1* | 3/2014 | Liu | ................. | A24F 47/008 131/329 |
| 2014/0190503 A1* | 7/2014 | Li | ................. | A61M 15/06 131/329 |
| 2015/0020826 A1* | 1/2015 | Liu | ................. | A24F 47/008 131/329 |
| 2015/0101622 A1* | 4/2015 | Liu | ................. | A24F 47/008 131/328 |
| 2015/0237914 A1* | 8/2015 | Han | ................. | A24F 47/008 131/329 |

* cited by examiner

*Primary Examiner* — Anthony Calandra
(74) *Attorney, Agent, or Firm* — PROI Intellectual Property US (57) ABSTRACT

The present invention provides a mini-double flavor electronic cigarette, which comprises a steel tube screw element, an upper steel tube, a battery contact, an insulated ring, an atomizer screw element, a double-hole connector, two disposable atomizers, a battery core and a PCB. Double channel output is adopted, two single disposable atomizers are heated at the same time, underwater sound is simulated via a loud speaker, and LOGO may be projected by a projecting module. The electronic cigarette is equipped with the loud speaker and the projecting module which breaks the regular trend of the electronic cigarette since the market is not equipped with similar loud speaker and projecting module at present.

7 Claims, 14 Drawing Sheets

MINI-DOUBLE FLAVOR ELECTRONIC CIGARETTE

FIELD OF THE INVENTION

The present invention relates to an electronic cigarette, and in particular, to a mini-double flavor electronic cigarette.

BACKGROUND OF THE INVENTION

Electronic cigarettes have been widely applied. The present application aims at providing an electronic cigarette having the following features: having two single atomizers which can be used singly and replaced randomly; capable of sounding while smoking, wherein the sound may be music or natural sound; and provided with an LED capable of displaying a customer logo, which is similar to projection.

SUMMARY OF THE INVENTION

To solve the problems of the prior art, the present invention provides a mini-double flavor electronic cigarette, comprising: a steel tube screw element, an upper steel tube, a battery contact, an insulated ring, an atomizer screw element, a double-hole connector, two disposable atomizers, a battery core and a PCB.

The disposable atomizer comprises a suction nozzle, an atomizing tube, an atomizing core, an insulated ring and an atomizing contact. The atomizing contact is arranged in the middle of the insulated ring. The insulated ring is arranged in the atomizing core. The anode and cathode of a battery are respectively and electrically connected with the atomizing contact and the atomizing core. The first end of the atomizing tube is pressed onto the atomizing core. The suction nozzle is covered on the second end of the atomizing tube. The PCB is connected with the atomizing contacts and the atomizing cores of the two disposable atomizers. The PCB is connected with the battery core.

The insulated ring is arranged in the atomizer screw element. The battery contact penetrates through the insulated ring. The above battery contact, insulated ring and atomizer screw element are divided into two groups. The two groups are respectively pressed into the two holes of the double-hole connector. The upper steel tube is pressed into the double-hole connector from the top. The steel tube screw element is sheathed on the upper of the upper steel tube. The atomizing contacts of the two disposable electronic cigarette atomizers are respectively connected with the battery contacts.

As a further improvement, the present invention further comprises a loud speaker, wherein the loud speaker is electrically connected with the PCB.

As a further improvement, the present invention further comprises a projecting module and an LED lamp, wherein the projecting module and the LED lamp are fixed at the bottom of the mini-double flavor electronic cigarette through a bracket.

As a further improvement, the present invention further comprises a first lens, a second lens, a film pressing element, a film, a film sleeve, a first convex lens, a second convex lens, a first shell, and a second shell. The film is arranged in the film sleeve. The film pressing element is pressed into the film sleeve, and then the first lens, the second lens, the film sleeve, the first convex lens and the second convex lens are arranged in the second shell in sequence. The first shell and the second shell are matched and connected.

As a further improvement, the present invention further comprises a key, wherein the key is electrically connected with the PCB.

As a further improvement, the PCB is fixed by a bracket.

As a further improvement, the present invention further comprises a suction nozzle, a suction nozzle inner insert, a suction nozzle insert, a footstock, and an atomizing plug. The suction nozzle inner insert is arranged in the suction nozzle. The suction nozzle inner insert penetrates through the footstock and is clamped with the footstock. The suction nozzle insert is connected with the suction nozzle inner insert. The suction nozzle insert is arranged in the footstock. The atomizing plug is arranged between the footstock and the disposable atomizer.

The present invention has the advantageous effects as follows.

Double channel output is adopted, two single disposable atomizers are heated at the same time, underwater sound is simulated via a loud speaker, and LOGO may be projected by a projecting module. The electronic cigarette is equipped with the loud speaker and the projecting module which breaks the regular trend of the electronic cigarette since the market is not equipped with similar loud speaker and projecting module at present.

DETAILED DESCRIPTION OF THE PREFERRED EMBODIMENTS

The present invention is further described by reference to the drawings hereunder.

Figure 1:
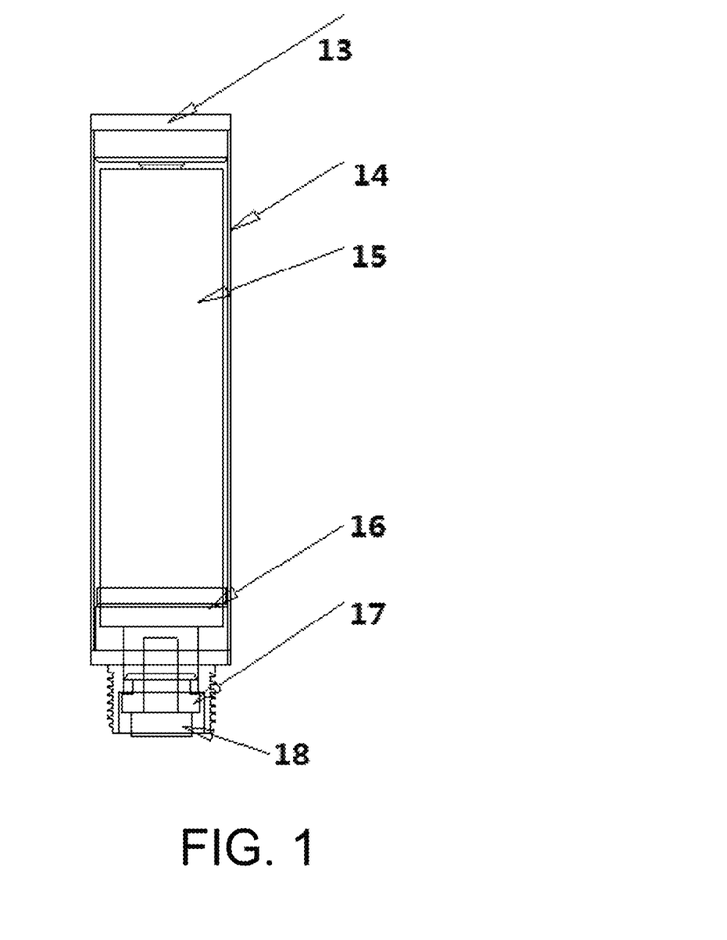
FIG. 1 is a structural schematic diagram of a disposable atomizer of the present invention.
Figure 2:
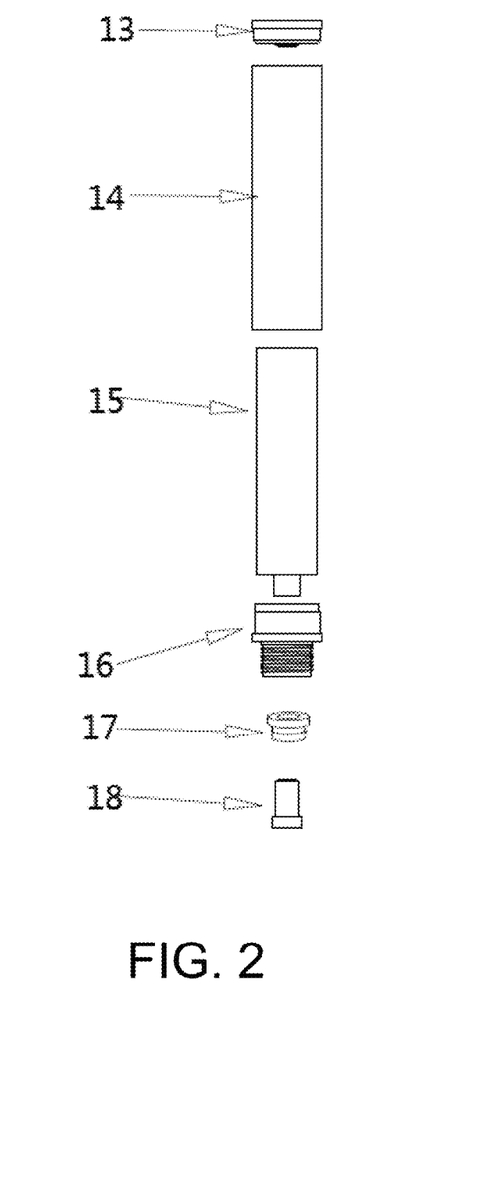
FIG. 2 is an exploded drawing of the disposable atomizer of the present invention.

FIG. 1 and FIG. 2 are the entire drawing and exploded drawing of a disposable electronic cigarette atomizer, wherein the disposable atomizer comprises a suction nozzle 13, an atomizing tube 14, an atomizing core 16, an insulated ring 17 and an atomizing contact 18. The atomizing contact 18 is arranged in the middle of the insulated ring 17. The insulated ring 17 is arranged in the atomizing core 16. The anode and cathode of a battery 15 are respectively and electrically connected with the atomizing contact 18 and the atomizing core 16. The first end of the atomizing tube 14 is pressed onto the atomizing core 16. The suction nozzle 13 is covered on the second end of the atomizing tube 14.

Figure 3:
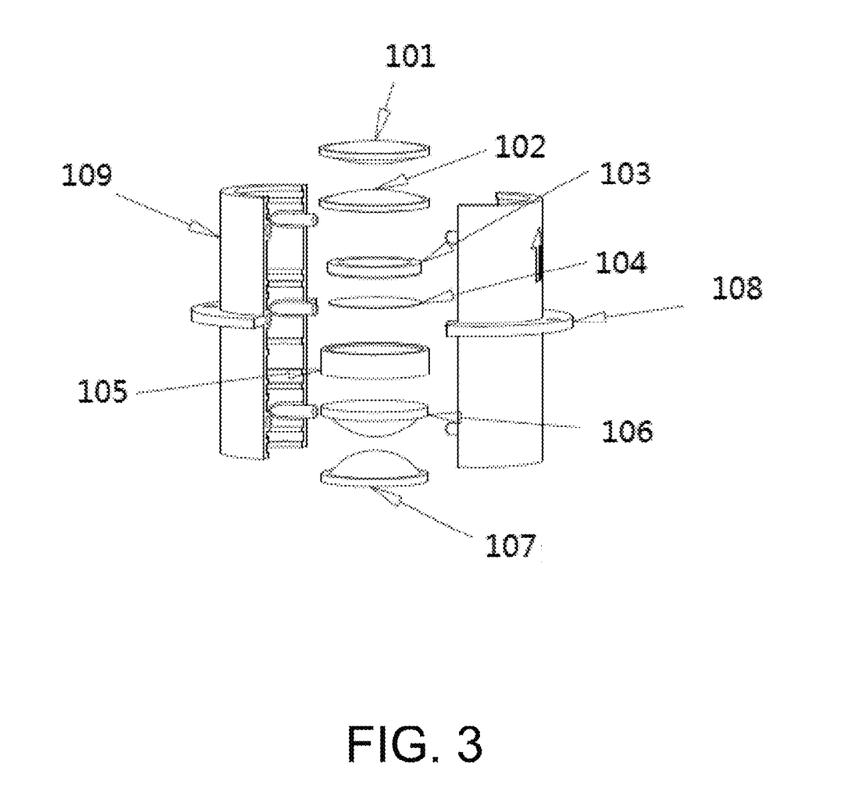
FIG. 3 is an exploded drawing of a projecting module of the present invention.

FIG. 3 is an exploded drawing of a projecting module of the present invention. As shown in FIG. 3, the film 104 is arranged in the film sleeve 105. The film pressing element 103 is pressed into the film sleeve 105, and then the first lens 101, the second lens 102, the film sleeve 105, the first convex lens 106 and the second convex lens 107 are arranged in the second shell 109 in sequence. The first shell 108 and the second shell 109 are matched and connected.

Figure 6:
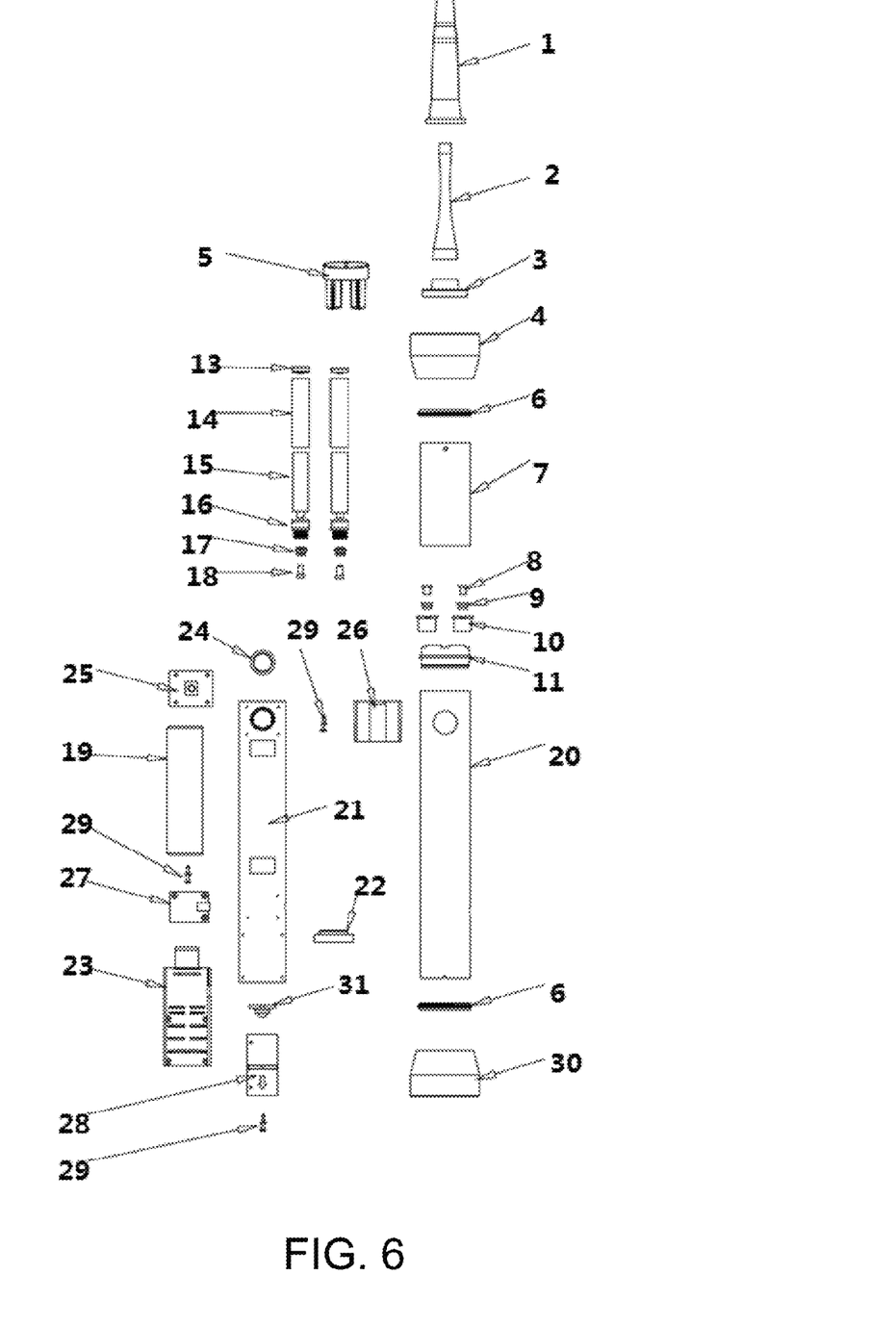
FIG. 6 is a structural schematic diagram of an exploded drawing of the present invention.

As shown in FIG. 6, a battery core 19, a loud speaker 22, a first PCB 25, a key bracket 26, a second PCB 27, a projecting module 28, an LED lamp 31, and a short bracket 23 are respectively arranged on the fixed positions of a long bracket 21. The key bracket 26 is arranged between a lower steel tube 20 and the long bracket 21. The key 24 is arranged on the key bracket 26. The key 24 is electrically connected with the first PCB 25. The first PCB 25 and the second PCB 27 are respectively fixed on the corresponding positions of the upper and the middle of the long bracket 21 through screw 29. The projecting module 28 is fixed on the long bracket 21 and the short bracket 23 through screw 29. The long bracket 21 and the short bracket 23 are arranged in the lower steel tube 20. Moreover, the bottom of the lower steel tube 20 and the steel tube screw element 6 are matched and connected. The bottom of the lower steel tube 20 and the steel tube screw element 6 are arranged in a base 30. The loud speaker 22, the LED lamp 31, the projecting module 28 and the battery core 19 are all arranged in the long bracket 21. A short bracket 23 is also provided. The long bracket and the short bracket wrap the loud speaker 22, the LED lamp 31, the projecting module 28 and the battery core 19 for fixation. The loud speaker 22 and the LED lamp 31 are respectively and electrically connected with the second PCB 27. The first PCB 25 and the second PCB 27 are electrically connected and are connected with the battery core 19. The first PCB 25 is connected with the atomizing contacts 18 and the atomizing cores 16 of the two disposable atomizers.

The insulated ring 9 is arranged in the atomizer screw element 10. The battery contact 8 penetrates through the insulated ring 9. The above battery contact 8, insulated ring 9 and atomizer screw element 10 are divided into two groups. The two groups are respectively pressed into the two holes of the double-hole connector 11. The upper steel tube 7 is pressed into the double-hole connector 11 from the top. The steel tube screw element 6 is sheathed on the upper of the upper steel tube 7.

The atomizing contacts 18 of the two disposable electronic cigarette atomizers are respectively connected with the battery contacts 8.

The suction nozzle inner insert 2 is arranged in the suction nozzle 1. The suction nozzle inner insert 2 penetrates through the footstock 4 and is clamped with the footstock 4. The suction nozzle insert 3 is connected with the suction nozzle inner insert 2. The suction nozzle insert 3 is arranged in the footstock 4.

The atomizing plug 5 is arranged between the footstock 4 and the atomizer.

Figure 7:
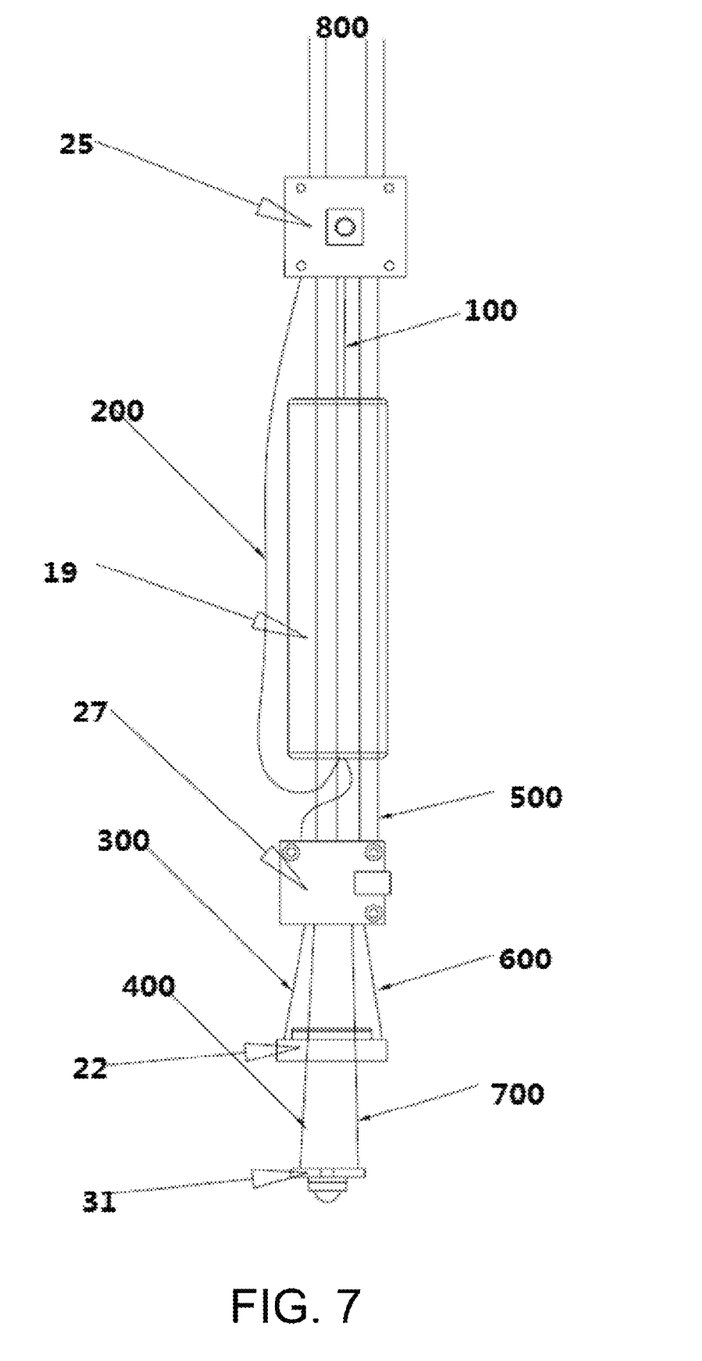
FIG. 7 is a schematic diagram of an electric connection relationship between partial parts of the present invention.

In FIG. 7, the first PCB 25 is respectively connected with the anode and the cathode of the battery core, wherein 100 refers to a line that connects the first PCB 25 with the anode of the battery core, and 200 refers to a line that connects the first PCB 25 with the cathode of the battery core. The second PCB 27 is respectively connected with the anode and the cathode of the loud speaker, wherein 300 refers to a line that connects the second PCB 27 with the cathode of the loud speaker, and 600 refers to a line that connects the second PCB 27 with the anode of the loud speaker. The second PCB 27 is respectively connected with the anode and the cathode of the LED lamp, wherein 400 refers to a line that connects the second PCB 27 with the cathode of the LED lamp, and 700 refers to a line that connects the second PCB 27 with the anode of the LED lamp. The first PCB 25 and the second PCB 27 are electrically connected, wherein 500 refers to four lines that connect the first PCB 25 with the second PCB 27. The first PCB 25 is electrically connected with the atomizing cores 16 and the atomizing contacts 18 of the two disposable atomizers, wherein 800 refers to four lines that connect the first PCB 25 with the atomizing cores 16 and the atomizing contacts 18 of the two disposable atomizers.

The assembly process is shown as follows.

As shown in FIG. 2, the insulated ring 17 is assembled into the atomizing core 16. The atomizing contact 18 is inserted into the middle of the insulated ring 17. The anode and the cathode of the battery 15 are respectively welded on the atomizing contact 18 and the atomizing core 16. Then one end of the atomizing tube 14 is pressed onto the atomizing core 16, and the suction nozzle 13 is covered on the other end of the atomizing tube to finish the assembly of the components.

Figure 4:
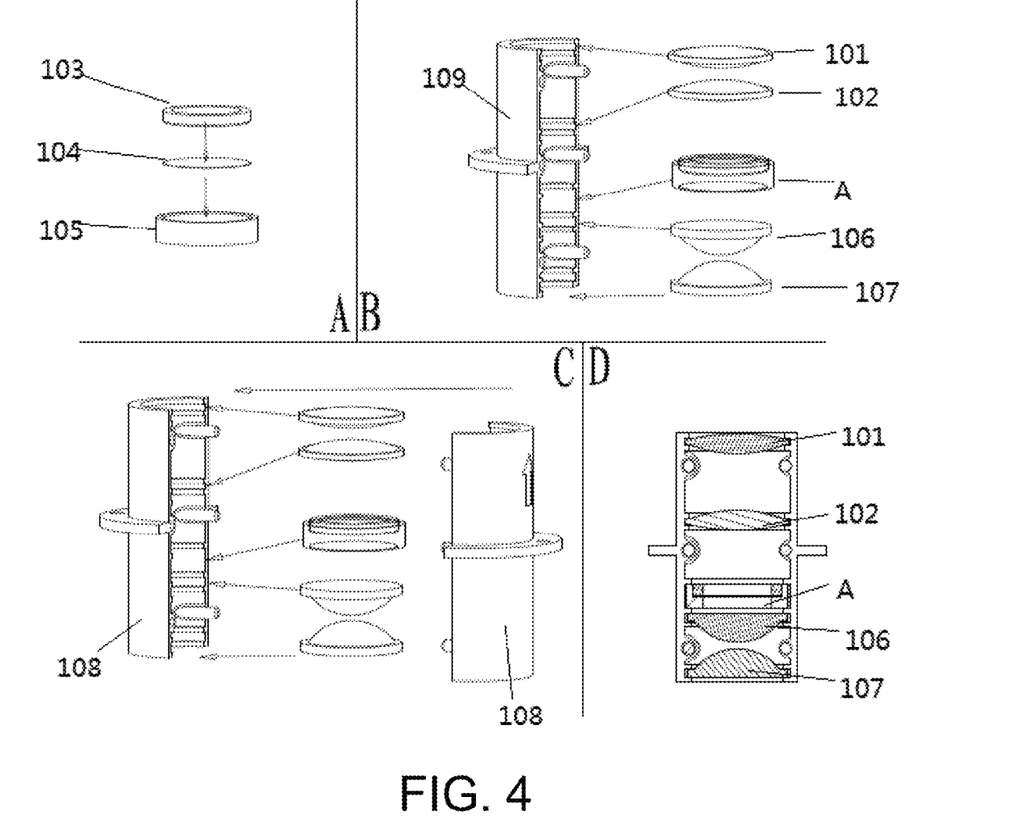
FIG. 4 is an assembly drawing of the projecting module of the present invention.

FIG. 4 is an assembly drawing of the projecting module of the present invention. As shown in FIG. 4, the film 104 is arranged in the film sleeve 105. The film pressing element 103 is pressed into the film sleeve 105 to finish the Fig. A in the assembly drawing. Then the first lens 101, the second lens 102, the Fig. A, the first convex lens 106 and the second convex lens 107 are arranged in the second shell 109 in sequence. The first shell 108 is inserted into the second shell 109 to finish the assembly of the components.

As shown in FIG. 5A to FIG. 5K, the battery core 19, the loud speaker 22, the key 24, the first PCB 25, the second PCB 27, the projecting module 28, the LED lamp 31 and the short bracket 23 are respectively mounted on the fixed positions of the long bracket 21 in sequence. The first PCB 25 and the second PCB 27 are respectively tightened up on the corresponding positions of the upper and the middle of the long bracket 21 through screw 29. The projecting module 28 is tightened up on the long bracket 21 and the short bracket 23 through screw 29 to finish FIG. 5A.

Figure 5A:
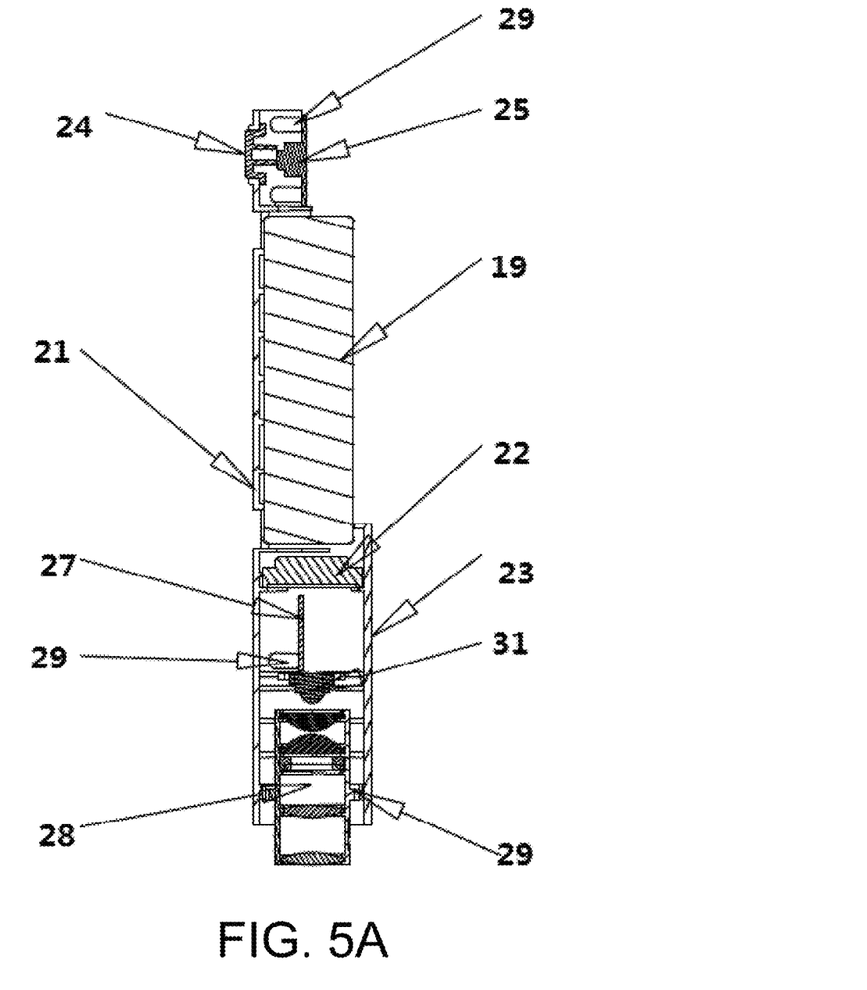
FIGS. 5A-5K are structural schematic diagrams for assembling the present invention.
Figure 5B:
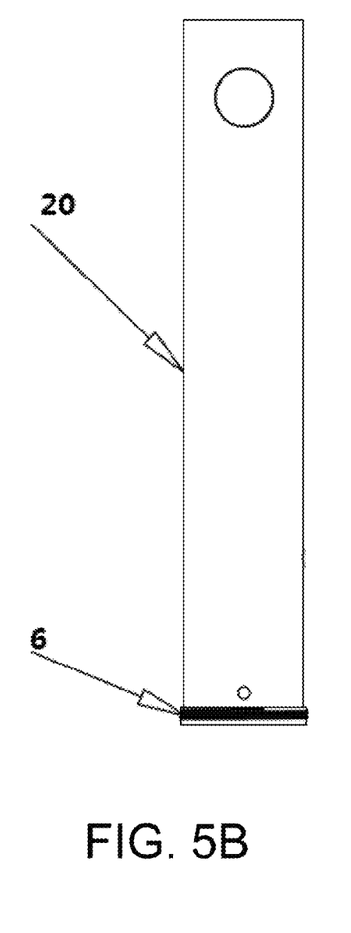

The steel tube screw element 6 is pressed to the lower steel tube 20 along a fixed direction, thus finishing FIG. 5B.

Figure 5C:
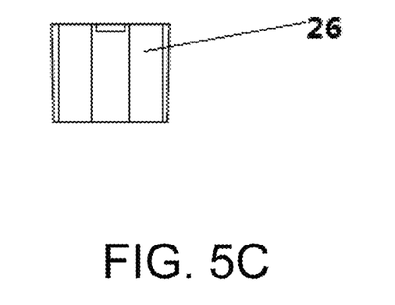
Figure 5D:
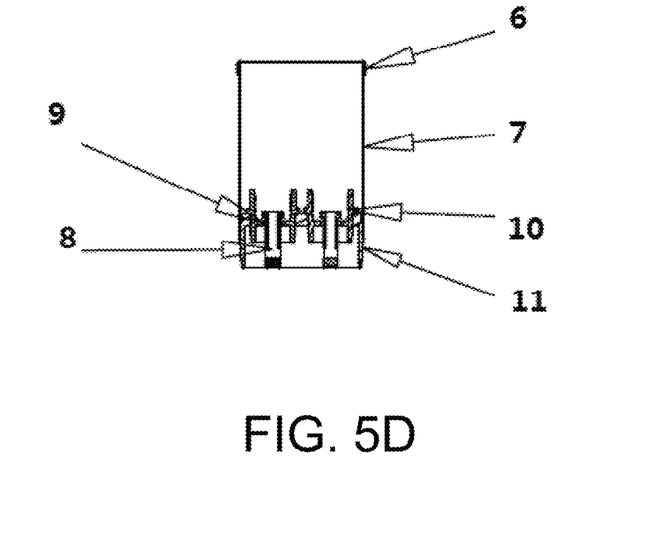

The key bracket 26 and the base 30 as shown in Fig. C and Fig. H are prepared.

Figure 5E:
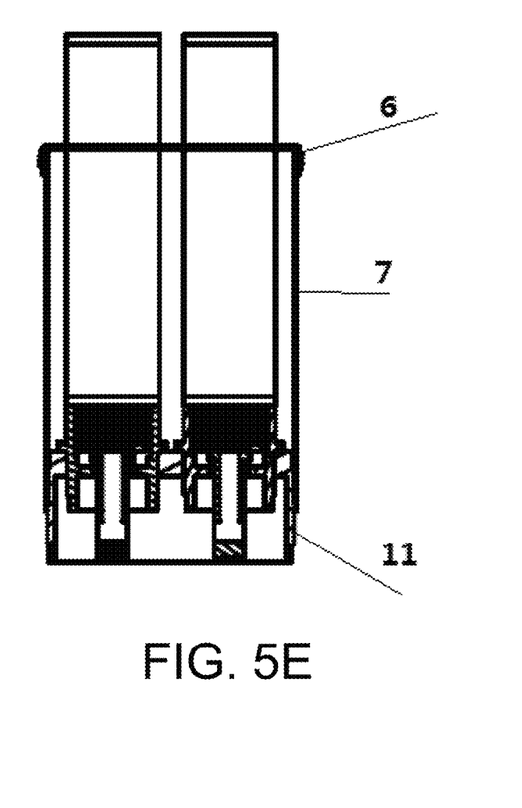
Figures 5F, 5G:
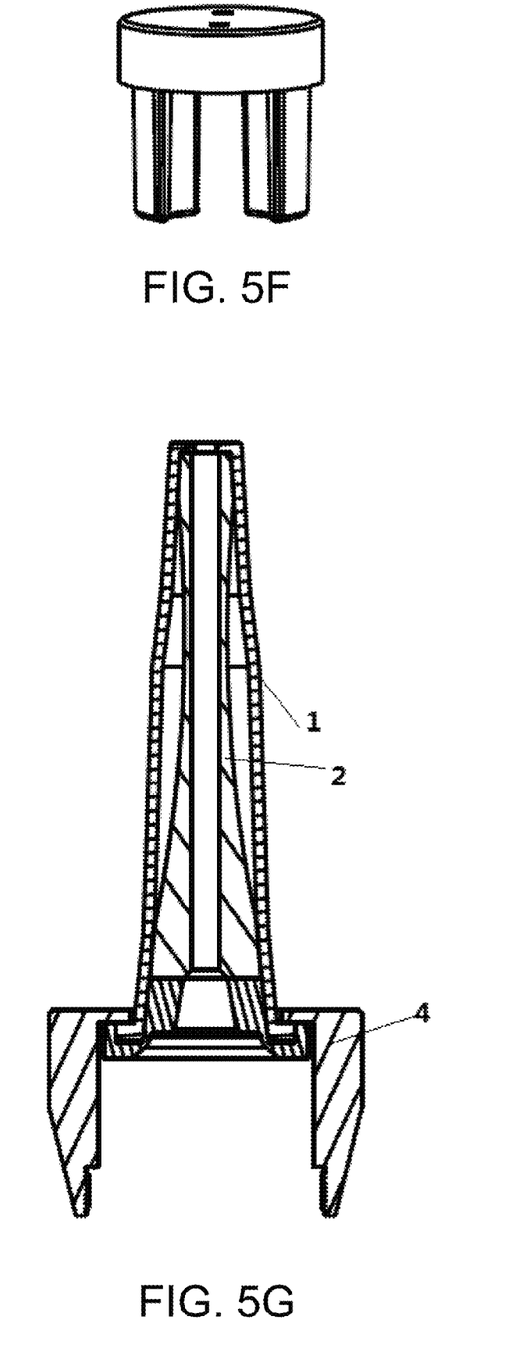
Figure 5H:
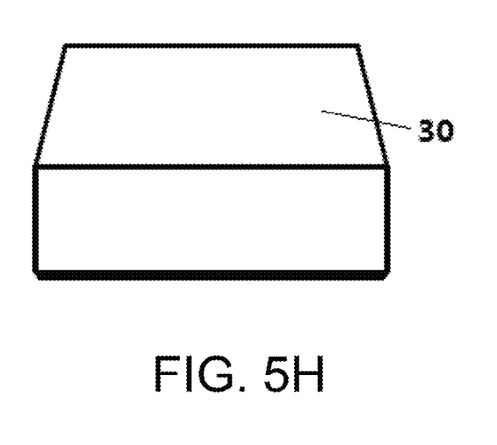
Figure 5I:
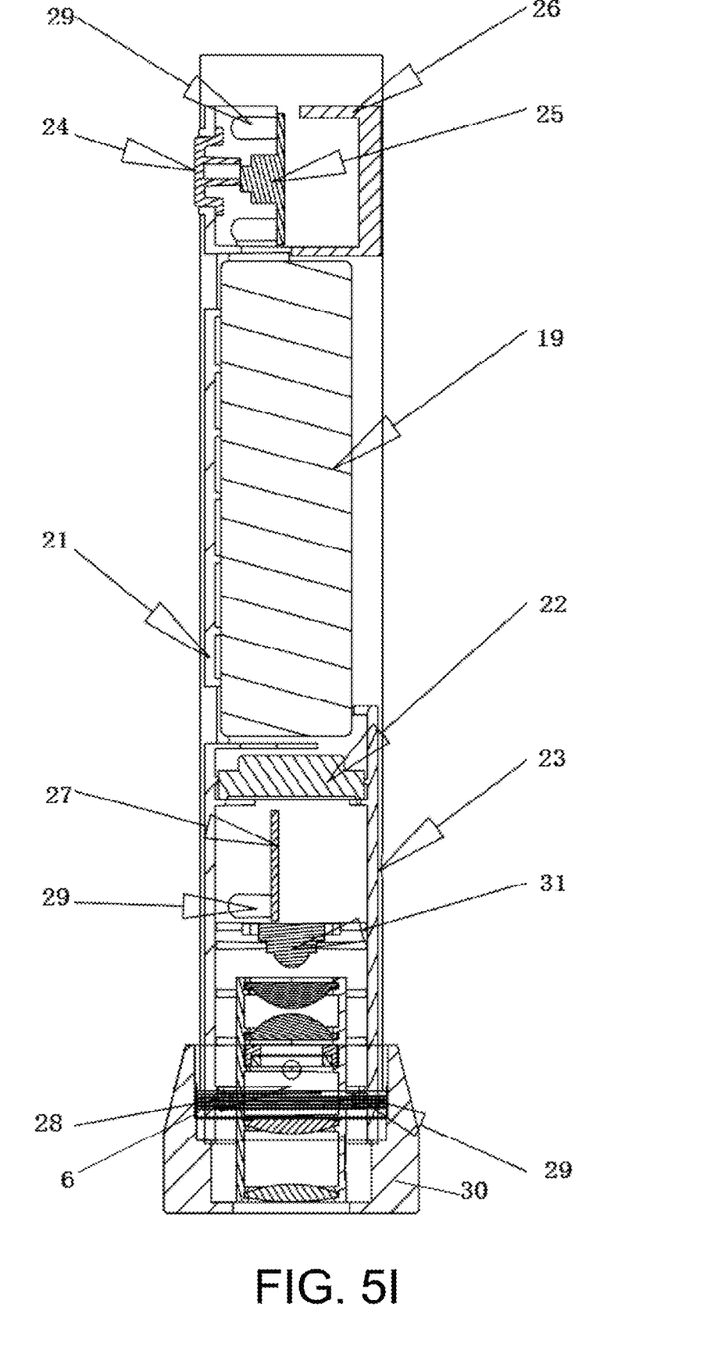

In FIG. 5I, the components assembled according to Fig. A are mounted in the component as shown in Fig. B. The prepared key bracket 26 is mounted between the lower steel tube 20 and the long bracket 21. The base 30 is matched with the screw thread of the steel tube screw element 6 mounted onto the lower steel tube 20, and screwed to a position that the base cannot be screwed, thus being capable of obtaining FIG. 5I.

The insulated ring 9 is mounted to the atomizer screw element 10, and then the battery contact 8 is penetrated through the insulated ring 9. Two of the assembled components are prepared and respectively pressed into the two holes of the double-hole connector 11. Then the upper steel tube 7 is pressed into the double-hole connector 11 from the top, and the steel tube screw element 6 is sheathed on the upper of the upper steel tube 7, thus being capable of obtaining FIG. 5D.

Two assembled 510 disposable electronic cigarette atomizers are respectively mounted onto the component assembled according to the assembly drawing 5D, thus being capable of obtaining FIG. 5E.

The suction nozzle inner insert 2 is mounted in the suction nozzle 1 and then is sheathed in the footstock 4. Then the suction nozzle insert 3 is taken out and pressed into the footstock 4 from the bottom, thus being capable of obtaining FIG. 5G.

Figure 5J:
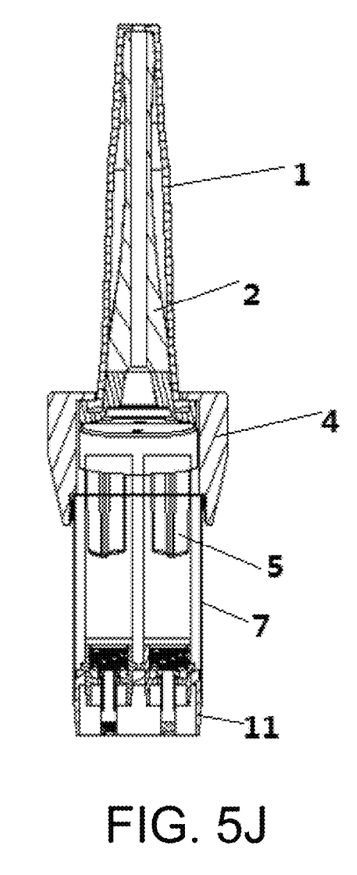

The atomizing plug 5 is sheathed on the assembled component as shown in Fig. E, and then the component as shown in Fig. G is connected onto the component as shown in Fig. E through screw, thus being capable of obtaining FIG. 5J.

Figure 5K:
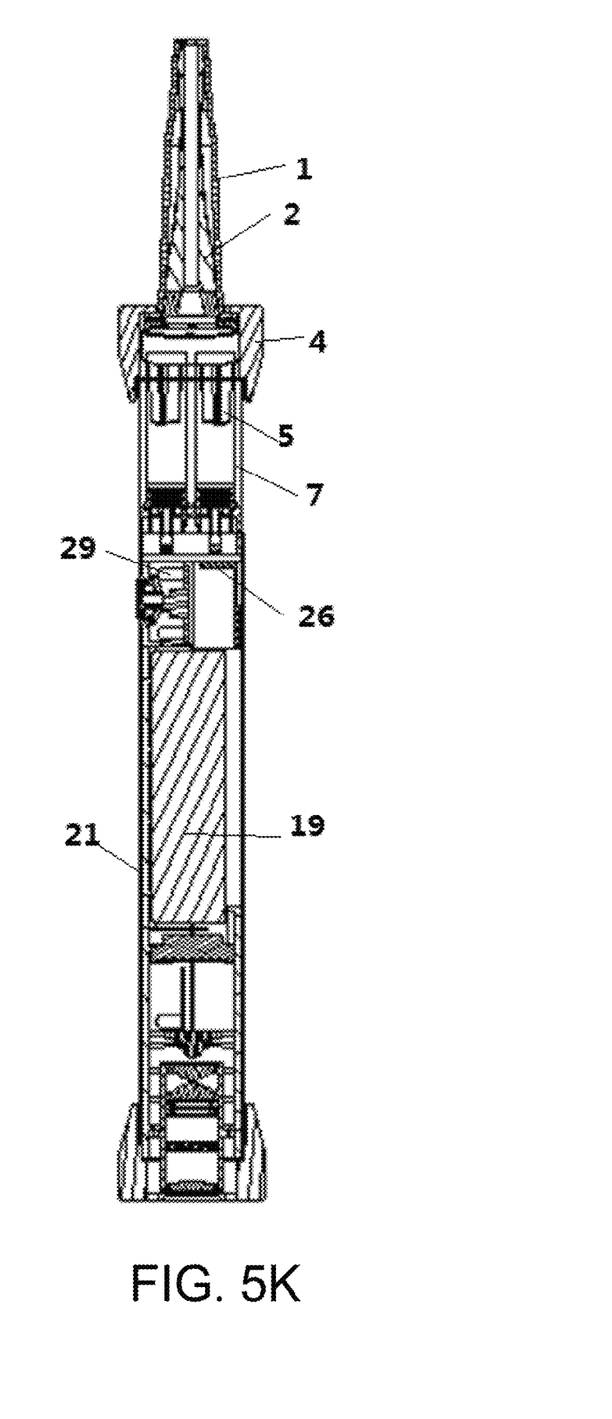

The component as shown in Fig. J is pressed onto the component as shown in Fig. I, to obtain FIG. 5K, thus finishing the assembly of the entire product.

The foregoing contents are further descriptions to the present invention by reference to the specific embodiments, but are not deemed to limit the specific embodiments of the present invention to these descriptions. A person having ordinary skill in the art may also make a plurality of simple deductions or replacement without departing from the concept of the present invention, which shall all fall within the protection scope of the present invention.

What is claimed is:

1. A mini-double flavor electronic cigarette, comprising a steel tube screw element (6), an upper steel tube (7), a battery contact (8), an insulated ring (9), an atomizer screw element (10), a double-hole connector (11), two disposable atomizers, a battery core (19) and a PCB; wherein the disposable atomizer comprises a suction nozzle (13), an atomizing tube (14), an atomizing core (16), an insulated ring (17) and an atomizing contact (18); the atomizing contact (18) is arranged in the middle of the insulated ring (17); the insulated ring (17) is arranged in the atomizing core (16); the anode and cathode of a battery (15) are respectively and electrically connected with the atomizing contact (18) and the atomizing core (16); the first end of the atomizing tube (14) is pressed onto the atomizing core (16); the suction nozzle (13) is covered on the second end of the atomizing tube (14); the PCB is connected with the atomizing contacts (18) and the atomizing cores (16) of the two disposable atomizers; and the PCB is connected with the battery core (19);

the insulated ring (9) is arranged in the atomizer screw element (10); the battery contact (8) penetrates through the insulated ring (9); the above battery contact (8), insulated ring (9) and atomizer screw element (10) are divided into two groups; the two groups are respectively pressed into the two holes of the double-hole connector (11); the upper steel tube (7) is pressed into the double-hole connector (11) from the top; the steel tube screw element (6) is sheathed on the upper of the upper steel tube (7); and the atomizing contacts (18) of the two disposable electronic cigarette atomizers are respectively connected with the battery contacts (8).

2. The mini-double flavor electronic cigarette according to claim 1, further comprising:
a loud speaker (22), wherein the loud speaker (22) is electrically connected with the PCB.

3. The mini-double flavor electronic cigarette according to claim 1, further comprising:
a projecting module (28) and an LED lamp (31), wherein the projecting module (28) and the LED lamp (31) are fixed at the bottom of the mini-double flavor electronic cigarette through a bracket.

4. The mini-double flavor electronic cigarette according to claim 3, wherein: the projecting module (28) comprises a first lens (101), a second lens (102), a film pressing element (103), a film (104), a film sleeve (105), a first convex lens (106), a second convex lens (107), a first shell (108) and a second shell (109); the film (104) is arranged in the film sleeve (105); the film pressing element (103) is pressed into the film sleeve (105), and then the first lens (101), the second lens (102), the film sleeve (105), the first convex lens (106) and the second convex lens (107) are arranged in the second shell (109) in sequence; the first shell (108) and the second shell (109) are matched and connected.

5. The mini-double flavor electronic cigarette according to claim 1, further comprising a key (24), wherein the key (24) is electrically connected with the PCB.

6. The mini-double flavor electronic cigarette according to claim 1, wherein: the PCB is fixed by a bracket.

7. The mini-double flavor electronic cigarette according to claim 1, further comprising a suction nozzle (1), a suction nozzle inner insert (2), a suction nozzle insert (3), a footstock (4), and an atomizing plug (5); the suction nozzle inner insert (2) is arranged in the suction nozzle (1); the suction nozzle inner insert (2) penetrates through the footstock (4) and is clamped with the footstock (4); the suction nozzle insert (3) is connected with the suction nozzle inner insert (2); the suction nozzle insert (3) is arranged in the footstock (4); and the atomizing plug (5) is arranged between the footstock (4) and the disposable atomizer.

* * * * *